(12) United States Patent
Evans et al.

(10) Patent No.: US 6,372,925 B1
(45) Date of Patent: Apr. 16, 2002

(54) PROCESS FOR OPERATING THE EPOXIDATION OF ETHYLENE

(75) Inventors: Wayne Errol Evans, Richmond; Peter Ingraham Chipman, Houston, both of TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/735,360

(22) Filed: Dec. 12, 2000

Related U.S. Application Data

(63) Continuation-in-part of application No. 09/591,525, filed on Jun. 9, 2000, now abandoned.

(51) Int. Cl.[7] .......................................... C07D 301/10
(52) U.S. Cl. ...................................... 549/536; 549/534
(58) Field of Search ................................. 549/534, 536

(56) References Cited

U.S. PATENT DOCUMENTS

| | | | |
|---|---|---|---|
| 3,960,775 A | 6/1976 | Piccinini et al. ............ | 252/463 |
| 5,011,807 A | 4/1991 | Hayden et al. .............. | 502/218 |
| 5,099,041 A | 3/1992 | Hayden et al. .............. | 549/536 |
| 5,177,225 A | 1/1993 | Ramachandran et al. ... | 549/534 |
| 5,262,551 A | 11/1993 | Horrell, Jr. et al. ......... | 549/534 |
| 5,380,697 A | * 1/1995 | Matusz et al. .............. | 502/348 |

FOREIGN PATENT DOCUMENTS

| | | | |
|---|---|---|---|
| EP | 0266015 | * | 5/1988 |
| EP | 0567273 | * | 10/1993 |
| GB | 1191983 | | 5/1970 |

* cited by examiner

*Primary Examiner*—Ba K. Trinh

(57) ABSTRACT

There is provided a process for the vapor phase oxidation of ethylene to ethylene oxide in the presence of a supported highly selective silver-based catalyst, the process comprising operating fresh catalyst for an initial operation phase, then operating at a further operation phase when the catalyst has reached an advanced aged defined by a cumulative ethylene oxide production exceeding 1.5 kT EO per $m^3$ of catalyst. In the further operation phase the composition of the reaction mixture is changed to contain from 1.1 to 4 times the concentration of ethylene used in the initial operation phase and the corresponding optimised and safe concentration of oxygen.

11 Claims, 2 Drawing Sheets

PROCESS FOR OPERATING THE EPOXIDATION OF ETHYLENE

This application is a continuation in part of Ser. No. 09/591,525 filed Jun. 9, 2000, now abandoned.

FIELD OF THE INVENTION

The present invention relates to a process for operating the vapor phase epoxidation of ethylene in the presence of a supported Highly Selective silver based catalyst. More particularly, it relates to an improved process for ethylene epoxidation wherein, in the course of operation, consequences of catalyst aging are offset.

BACKGROUND OF THE INVENTION

In the catalytic epoxidation of ethylene, modern silver-based supported catalysts are highly selective towards ethylene oxide production. Under certain operation conditions their selectivity towards ethylene oxide, expressed as a percentage of the ethylene converted, can reach values above the 6/7 or 85.7 mol % limit which formerly—based on the reaction formula 7 $C_2H_4 + 6O_2 \rightarrow 6C_2H_4O + 2CO_2 + 2H_2O$, see Kirk-Othmer's *Encyclopedia of Chemical Technology*, $3^{rd}$ ed. vol 9 (1980) p. 445—was considered to be the theoretically maximal selectivity of this reaction. Such Highly Selective catalysts, comprising as their active components silver, rhenium, at least one further metal and optionally a rhenium co-promoter, are disclosed in EP-B 0 266 015 and in several subsequent patent publications.

Like all catalysts, the Highly Selective silver based ethylene epoxidation catalysts are subject to aging-related performance decline during normal operation and they need to be exchanged periodically. The aging manifests itself by a reduction in both selectivity and activity performance of the catalyst. Selectivity and activity are the primary (although not the only) determinants of plant profitability. There exists, therefore, a considerable economic incentive for delaying the need for exchanging the catalyst by preserving these values as long as possible. Several patent publications are known which are directed at stabilizing the catalyst by introducing modifications in the catalyst composition or in the support material, but thus far the reaction conditions and, in particular the feed composition, escaped attention in this respect.

It is known in general that when the concentration of ethylene and/or of oxygen in the reactor feed gas is increased, both activity and selectivity of the ethylene epoxidation reaction can improve.

In EP-A 567 273 there is disclosed a process for the production of ethylene oxide in the presence of a silver metal catalyst and halide gas phase inhibitor in a reaction zone, characterized by the introduction into the reaction zone of a feed gas mixture comprising 30 to 90 mol % ethylene, 2 to 10 mol % oxygen and 1 to 50 ppm organic halide gas phase inhibitor, the temperature in the reaction zone being maintained between 180 and 350° C. The Examples of the reference show a small improvement in selectivity and a greater improvement in activity occurring during 15 to 20 operation hours, as the concentration of ethylene is raised from 30 mol % through 45 and 60 mol % up to 75 mol %—the concentration of oxygen being kept constant at 8 mol % in all cases and the composition of the catalyst not being specified.

However, it is also known that in actual practice in order to remain outside the flammability limit of the gas mixture the concentration of oxygen has to be lowered as the concentration of ethylene is raised. The actual safe operating ranges depend, along with the gas composition (reactants and balance gases), also on individual plant conditions such as temperature and pressure. Therefore in each individual plant a so-called flammability equation is used to determine the concentration of oxygen which may be used with any given concentration of ethylene. This flammability equation can be expressed graphically in a so-called flammability curve.

The fact that in the examples of EP-A 0 567 273 the oxygen concentration was kept constant while the ethylene concentration was raised makes these examples unrealistic as regards actual plant conditions. It implies that either the oxygen concentration used with the lowest ethylene concentration level was sub-maximal (in which case the performance at this lowest ethylene concentration level was actually sub-optimal), or the oxygen concentration used with the higher ethylene levels was above the flammability limit (in which case the improved experimental results cannot be carried over to commercial plant operation). Either way, this may throw some doubt on the relevance of the showing of higher performance at the higher ethylene concentrations, since the different ethylene concentrations exemplified were not compared at their respective maximum allowable oxygen levels. Moreover it is to be noted that fresh catalysts of an unspecified composition were used in these examples, during only 15 or 20 operating hours.

It has now been found that aged Highly Selective ethylene oxidation catalysts react differently to the composition of the reactant gas mixture than do fresh Highly Selective ethylene oxidation catalysts. More specifically, with the fresh Highly Selective catalysts the selectivity of the reaction towards ethylene oxide is not influenced substantially when a higher concentration of ethylene is combined with a lower (i.e. safe) concentration of oxygen, while with the aged Highly Selective catalysts the selectivity under these conditions is substantially improved. Differences of activity performance under conditions of raised ethylene concentration and lowered oxygen concentration between fresh and aged Highly Selective catalysts are in the same direction but less pronounced. By contrast to the highly selective catalysts it has been found that aged and fresh traditional ethylene oxidation catalysts, i.e. catalysts whose selectivity does not reach the level of 6/7 or 85.7%, do not exhibit this clear difference in their reaction to the composition of the feed gas mixture.

SUMMARY OF THE INVENTION

The present invention therefore provides a process for the vapor phase oxidation of ethylene to ethylene oxide in the presence of a supported highly selective silver-based catalyst, at a work rate w in the range of from 32 to 320 kg ethylene oxide produced per $m^3$ of catalyst per hour, the reaction mixture containing ethylene, oxygen, optional carbon dioxide, gas phase moderator and balance inert gases, the reaction temperature being from 180 to 325° C., the reactor inlet pressure from 1000 to 3500 kPa and the GHSV from 1500 to 10000, the process comprising:

operating at an initial operation phase wherein fresh catalyst is used, the reaction gas mixture containing an ethylene concentration which represents an economically optimized balance between catalyst performance (expressed, at the given work rate w, by the selectivity $S_w$ in mol % and by the operating temperature $T_w$ in ° C.) on the one hand and ethylene vent losses on the other, and an oxygen concentration which complies with safety-related flammability restrictions; and operating at a further operation phase when the catalyst has reached an advanced aged defined by a cumulative ethylene oxide production exceeding 1.5 kT EO per m$^3$ of catalyst, wherein in said further operation phase the composition of the reaction mixture is changed to contain from 1.1 to 4 times the concentration of ethylene used in the initial operation phase and the corresponding optimized and safe concentration of oxygen.

By raising the ethylene content of the reaction gas mixture, yet simultaneously reducing the oxygen content to remain below the flammability limit, both selectivity and activity of the aged High Selectivity catalyst are improved significantly.

DETAILED DESCRIPTION OF THE INVENTION

Figure 1:
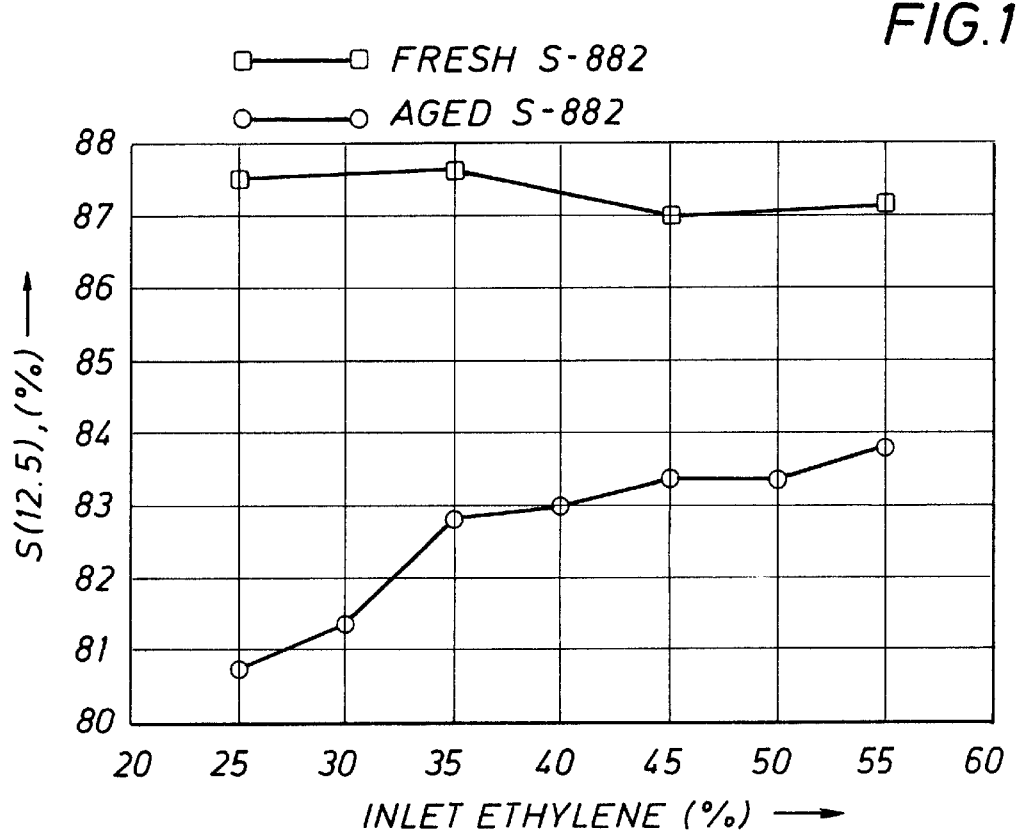
FIG. 1 shows the selectivity of a high selectivity catalyst versus the percent ethylene produced for aged and fresh catalyst.

As used herein, an "aged catalyst" means a catalyst which, in the course of operation, has reached an advanced aged defined by a cumulative ethylene oxide production exceeding 1.5 kT EO per m$^3$ of catalyst.

The vapor phase (direct) oxidation processes of ethylene to ethylene oxide can be air-based or oxygen-based, see Kirk-Othmer's *Encyclopedia of Chemical Technology*, 3rd ed. vol 9 (1980) p. 445–447. In the air-based processes air or air enriched with oxygen is fed directly to the system while in the oxygen-based processes high-purity (>95 mol %) oxygen is employed as the source of the oxidizing agent. Presently most ethylene oxide production plants are oxygen-based and this is the preferred embodiment of the present invention.

Both air-based and oxygen-based processes require the venting of a purge stream in order to avoid accumulation of inert gases, though the purge stream of the air-based process is much larger because of the large amount of nitrogen which is constantly introduced. In any case, at least some ethylene is always lost with the purge stream. The amount of ethylene lost in this way depends on the purge stream (which as indicated above is smaller in oxygen-based plants) but also on the concentration of ethylene in the reaction gas mixture. The technical and economical conditions (including the price of ethylene) determine for every individual plant an optimized balance between best catalyst performance and least ethylene vent losses.

"GHSV," or Gas Hourly Space Velocity, is the unit volume of gas at standard temperature and pressure passing over one unit volume of packed catalyst per hour.

The optimal ethylene concentration, calculated on the total of the reaction mixture, which is used with the fresh catalyst in the initial operation phase, depends on the plant, the catalyst, the reaction conditions and the work rate w chosen. Generally it will be in the range of from 2 to 40 mol % of ethylene, the concentration usually used with air operated plants ranging from 2 to 15 mol % and the concentration usually used in oxygen operated plants ranging from 15 to 40 mol % of ethylene. With the aged catalyst, in the further operation phase according to the present invention, the concentration of ethylene is raised to a level of from 1.1 to 4 times the concentration of ethylene used in the initial operation phase. More particularly it will be raised by from 5 to 30 mol % of ethylene, preferably by from 10 to 20 mol %.

The expression "the corresponding optimal concentration of oxygen" means the concentration of oxygen which, under the temperature and pressure conditions employed in the plant and combined with the chosen concentration of ethylene, secures optimal performance while avoiding the flammability limit. Generally, the concentration of oxygen used with fresh catalyst will be within the broad range of from 6 to 12 mol % of the total gas feed, and the concentration of oxygen used with aged catalyst according to the present invention will be lower than the concentration used with the fresh catalyst by 0.4 to 3.5 mol %, depending on the level to which the ethylene concentration is raised.

The maximal oxygen concentration, i.e. its flammability limit, which can be used with any given concentration of ethylene, is determined by the gas composition, the temperature and the pressure. More particularly, the oxygen flammability limit is reduced by the gas containing higher concentrations of ethylene, of ethylene oxide, and/or of argon, by a higher temperature and/or by a higher pressure employed—and it is increased by the gas containing higher concentrations of paraffins such as methane and/or ethane, of nitrogen, and/or Of $CO_2$.

Carbon dioxide is a by-product of the ethylene oxidation process. Since unconverted ethylene is continuously recycled, and since concentrations of $CO_2$ in the reactor feed which are much in excess of 15 mol % will have an adverse effect on catalyst activity, accumulation of $CO_2$ has to be avoided and $CO_2$ is continuously removed from the recycle gas. This is done by venting and by continuous absorption of the formed carbon dioxide. Currently concentrations of $CO_2$ as low as 1 mol % are practical, and in future even lower concentrations may be reached. The process of the present invention is independent of the presence or absence of $CO_2$ in the reaction mixture.

A gas phase catalyst moderator is added to the feed for selectively suppressing the undesirable oxidation of ethylene and of ethylene oxide to carbon dioxide and water. Many organic compounds, especially organic halides but also amines, organometallic compounds and aromatic hydrocarbons are known to be effective in this respect. Organic halides are the preferred gas phase catalyst moderators and they are effective without suppressing the desired reaction when used in concentrations ranging from 0.3 to 20 ppmv of the total volume of the feed gas.

The optimal concentration of gas phase catalyst moderator to be used in practice depends on plant conditions and on the type of catalyst used. Conventional catalysts have relatively flat selectivity curves for the moderator (i.e. their selectivity is almost invariant over a wide range of moderator concentrations), and this property does not change during prolonged operation of the catalyst. Therefore the concentration of the moderator can be more freely chosen and it can remain the same during the entire lifespan of the catalyst. By contrast the highly selective catalysts tend to exhibit relatively steep moderator selectivity curves (i.e. selectivity varies considerably with relatively small changes in moderator concentration, and exhibits a pronounced maximum at the most advantageous or optimum level of moderator). This moderator optimum, moreover, does tend to change during prolonged operation. Consequently, the moderator concentration has to be optimized repeatedly during operation if the maximum achievable selectivity is to be maintained.

Preferred organic halides are $C_1$ to $C_8$ chlorohydrocarbons or bromohydrocarbons. More preferably they are selected from the group of methyl chloride, ethyl chloride, ethylene chloride, ethylene dibromide, vinyl chloride or a mixture thereof. The most preferred gas phase catalyst moderator is ethyl dichloride.

The balance inert gases usually present in the reaction feed comprise varying concentrations of nitrogen, argon, and added saturated hydrocarbon such as methane or ethane. Since unconverted ethylene is continuously recycled, and oxygen added, the accumulation of balance gases has to be avoided. The process of the present invention is independent of the amount of balance inert gases in the reaction mixture.

The work rate w, which is the amount of ethylene oxide produced per unit volume of catalyst (kg per $m^3$, or gram per liter, etc.) per hour, is influenced by the temperature, the pressure and the gas velocity used. When comparing the effect of varying the catalyst and/or the gas composition on $T_w$ and $S_w$, the pressure and the gas velocity are to be kept constant.

The efficiency of the ethylene oxidation reaction and catalyst is defined by their selectivity and activity.

The value of the selectivity parameter $S_w$, expressed in mol % of the desired ethylene oxide formed relative to the total of ethylene converted at a given work rate w, will vary with the value of the actual work rate w. For example, $S_{200}$ is the selectivity at a work rate of 200 kg of ethylene produced per $m^3$ of catalyst per hour.

The value of the activity parameter $T_w$, which is the temperature needed to reach a given work rate w, will also vary with the value of w. For example, $T_{200}$ is the temperature needed to reach a work rate of 200 kg of ethylene produced per $m^3$ of catalyst per hour.

With both fresh and aged catalyst, the optimal ethylene concentration can be determined by successively measuring, at a fixed value of w, the performance in terms of $S_w$ and $T_w$ of progressively raised concentrations of ethylene, coupled with the corresponding safe concentrations of oxygen, until no further improvement can be reached.

The material of the support of the supported silver based catalysts can be selected from a wide range of conventional materials which are considered to be inert in the presence of the ethylene oxidation feeds, products and reaction conditions. Such conventional materials can be natural or artificial and they include the aluminum oxides, magnesia, zirconia, silica, silicon carbide, clays, pumice, zeolites and charcoal. Alpha alumina is the most preferred material to be used as the main ingredient of the porous support.

The support is porous and preferably has a surface area, as measured by the B.E.T. method, of less than 20 $m^2/g$ and more in particular from 0.05 to 20 $m^2/g$. Preferably the B.E.T. surface area of the support is in the range of 0.1 to 10, more preferably from 0.1 to 3.0 $m^2/g$. The B.E.T. method of measuring the surface area has been described in detail by Brunauer, Emmet and Teller in *J. Am. Chem. Soc.* 60 (1938) 309–316.

A Highly Selective supported silver-based catalyst according to the present invention is one which, when operated fresh, exhibits a theoretical selectivity at zero work rate, $S_0$, of at least 6/7 or 85.7%. The value of $S_0$ for a given catalyst is found by operating the catalyst in a range of work rates w, resulting in a range of selectivity values $S_w$ corresponding to the range of work rates w. These values $S_w$, are then extrapolated back to the theoretical value of S at zero work rate, by the use of standard curve-fitting algorithms, such as those provided with the MICROSOFT® Excel program.

Preferred supported Highly Selective silver-based catalysts to be used in the present invention are rhenium containing catalysts. Such catalysts are defined in EP-B 0 266 015. Broadly, they contain a catalytically effective amount of silver, a promoting amount of rhenium or compound thereof, a promoting amount of at least one further metal or compound thereof and optionally a co-promoting amount of a rhenium co-promoter which can be selected from one or more of sulfur, phosphorus, boron, and compounds thereof, on a refractory support. More specifically the at least one further metal of these rhenium containing catalysts is/are selected from the group of alkali metals, alkaline earth metals, molybdenum, tungsten, chromium, titanium, hafnium, zirconium, vanadium, thallium, thorium, tantalum, niobium, gallium and germanium and mixtures thereof. Preferably the at least one further metal is/are selected from the alkali metals such as lithium, potassium, rubidium and cesium and/or from the alkaline earth metals such as calcium and barium. Most preferably it is lithium, potassium and/or cesium.

Preferred amounts of the components of these catalysts are, when calculated as the element on the total catalyst:

silver from 10 to 300 g/kg, rhenium from 0.01 to 15 mmol/kg, further metal or metals from 10 to 3000 mg/kg, and optional rhenium co-promoter from 0.1 to 10 mmol/kg.

The following examples will illustrate the invention.

Part I: The Catalysts

Catalyst A was S-882, a commercial Shell catalyst of the High Selectivity type as defined in EP-B 0 266 015, containing rhenium promoter and rhenium co-promoter and having a theoretical selectivity $S_0$ of 93% in the fresh state.

Comparative Catalyst B was S-860, a commercial Shell catalyst of the conventional type as defined in U.S. Pat. No. 5,380,697, not containing rhenium and rhenium co-promoter and having a theoretical selectivity $S_0$ of 85% in the fresh state.

The above values of $S_0$ were determined by collecting a range of selectivities Sw at multiple space velocities, each time at 30% ethylene, 8% oxygen, 5% $CO_2$ and 14 bar for both catalysts, the reaction temperature being 260° C. for Catalyst A and 235° C. for Catalyst B—and extrapolating back to infinite space velocity (i.e. zero work rate).

Fresh and aged Catalyst A and Comparative Catalyst B were tested. The aged catalyst A was taken from a commercial plant where it had been used for 21 months, having produced a total of 2400 Kg of ethylene oxide per liter of catalyst. The aged Comparative Catalyst B was taken from a commercial plant where it had been used for 34 months, having produced a total of 4500 Kg of ethylene oxide per liter of catalyst. Both aged catalysts were taken from the heart of the respective reactor tubes. They were analyzed and found to be free of contaminates.

Part II: The Catalyst Test Procedure

In each experiment, 1 to 5 grams of crushed catalyst (0.8–1.4 mm) were loaded into a micro-reactor consisting of a 3 mm internal diameter stainless steel U-shaped tube. The U-shaped tube was immersed in a molten metal tin/bismuth bath (heat medium) and the ends were connected to a gas flow system. The weight of the catalyst and the inlet gas flow rate were adjusted to achieve a gas hourly space velocity of 3300 ml of gas per ml of catalyst per hour. The inlet gas pressure was 1600 kPa.

In each experiment, the effect on one fresh or aged catalyst of one of seven equally spaced concentrations of ethylene in the feed, ranging from 25 to 55 mol %, was tested under optimized further feed and temperature conditions. In the feed, the concentration of oxygen used in each experiment was the maximum allowed within the flammability limit and ranged from 9 to 6.5 mol %. The concentration of $CO_2$ was set to a typical level for each type of catalyst, i.e., 3.5% for the fresh highly selective catalyst, and 5.0% for the aged highly selective catalyst and for the conventional catalysts. The concentration of ethyl chloride was optimized over the range of 2.0–4.0 ppmv for the fresh highly selective catalyst, optimized over the range of 3.0–7.0 ppmv for the aged highly selective catalyst, and set at 2.5 ppmv for the fresh and aged conventional catalysts. Nitrogen ballast comprised the remainder of the bulk feed mixture. The temperature in each experiment was adjusted, by raising it gradually, to achieve a constant work rate w (mg of ethylene oxide produced per ml of catalyst per hour). In accordance with typical commercial practice, the constant work rate w was 200 kg/m³/hr for the fresh and aged S-882 catalyst and for the fresh S-860 catalyst, and 160 kg/m³/hr for the aged S-860 catalyst.

Part III: The Results

Figure 2:
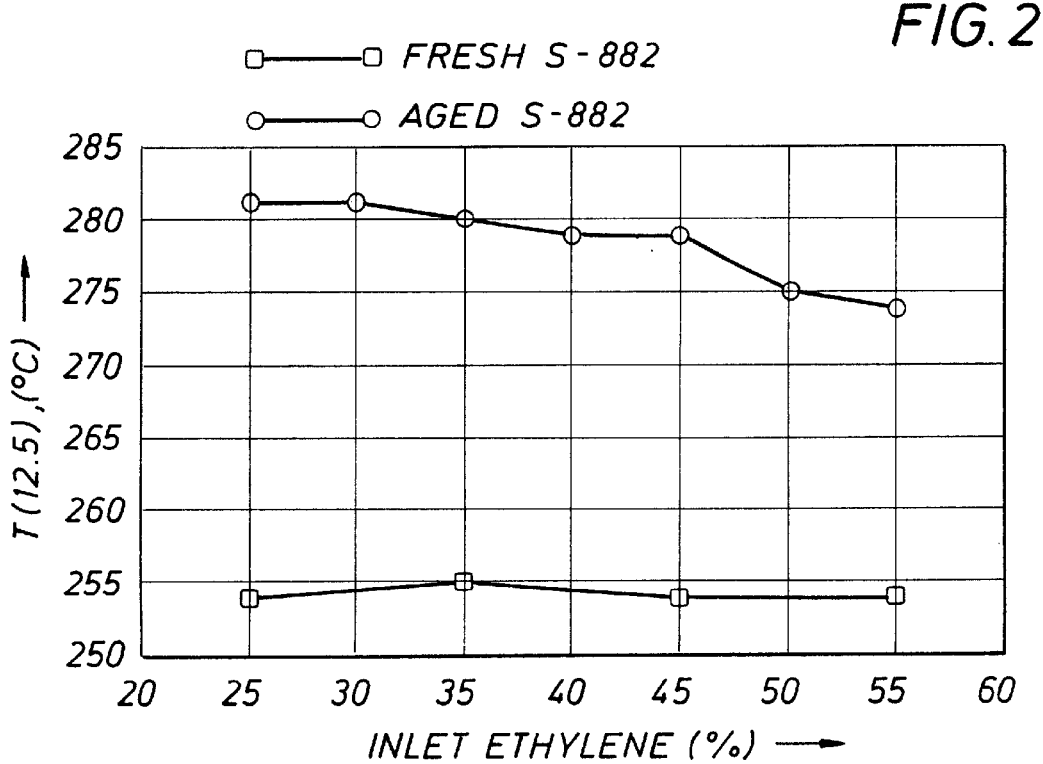
FIG. 2 shows the activity of a high selectivity catalyst versus the percent ethylene produced for aged and fresh catalyst.
Figure 3:
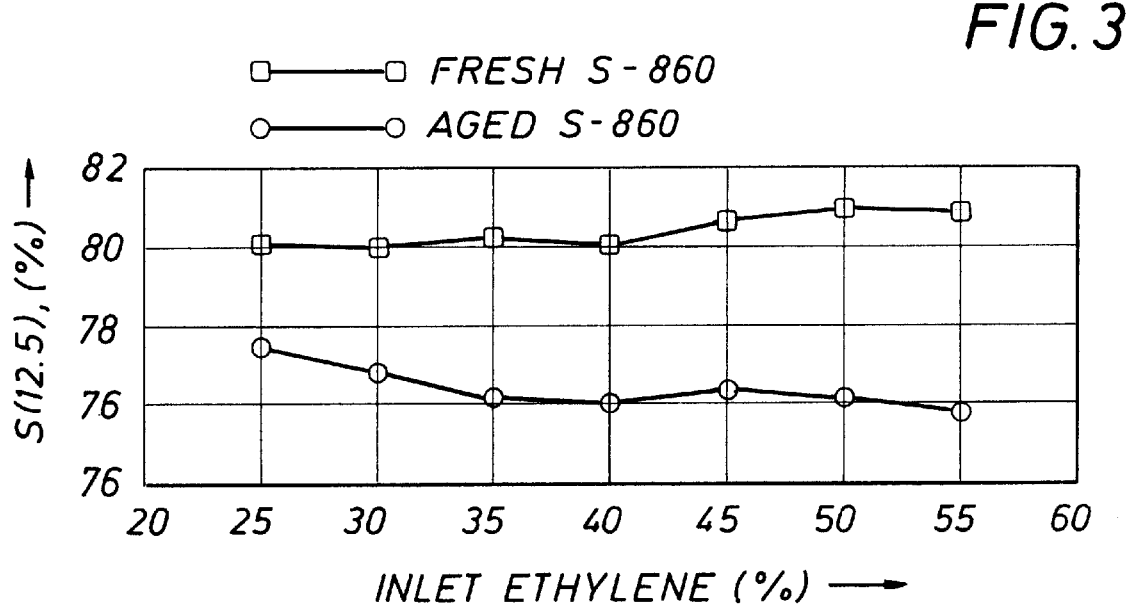
FIG. 3 shows the selectivity of a conventional catalyst versus the percent ethylene produced for aged and fresh catalyst.
Figure 4:
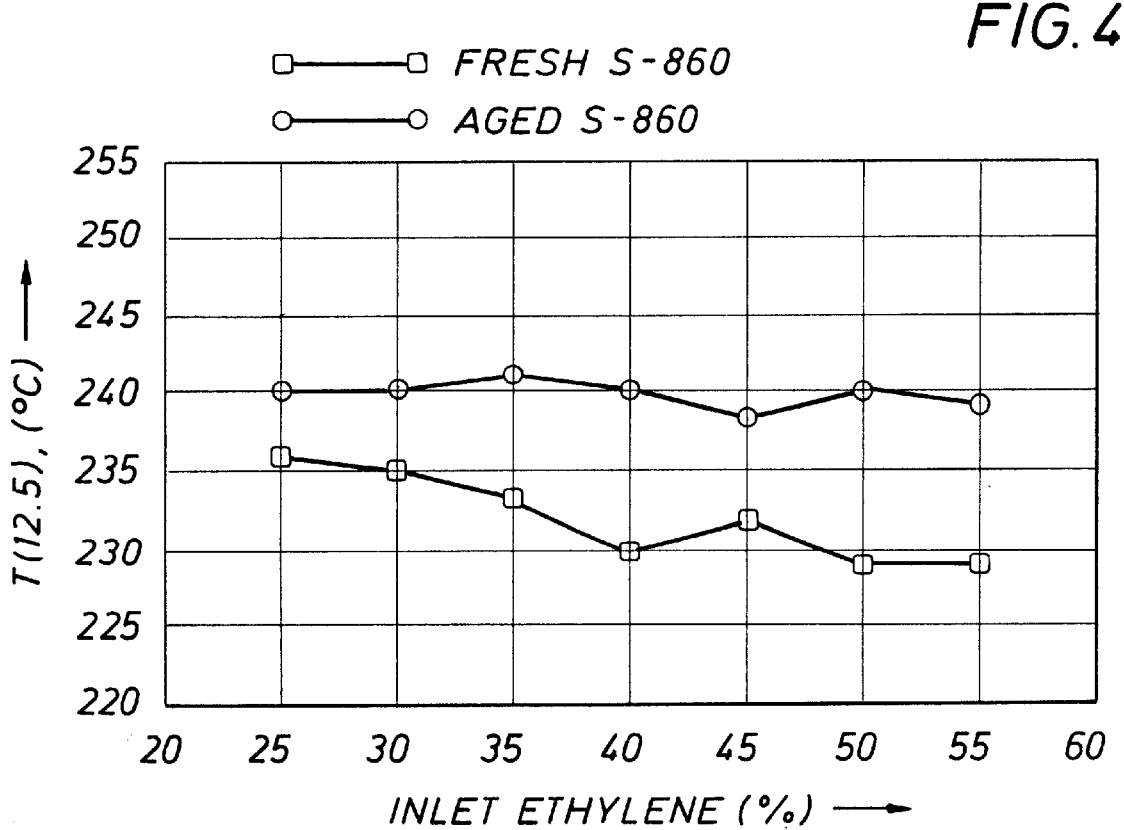
FIG. 4 shows the activity of a conventional catalyst versus the percent ethylene produced for aged and fresh catalyst.

The results are given in the following Table I and in FIGS. 1 to 4. In all the Figures, the percentage of oxygen was adjusted to conform with flammability.

TABLE I

| Example | Catalyst | $O_2$, mol % in feed | $C_2H_4$, mol % in feed | S (% EO) | T (° C.) |
|---|---|---|---|---|---|
| Comp. 1 | S-882, FRESH | 9.1 | 25 | 87.5 | 254 |
| Comp. 2 | S-882, FRESH | 8.2 | 35 | 87.6 | 255 |
| Comp. 3 | S-882, FRESH | 7.4 | 45 | 87.1 | 254 |
| Comp. 4 | S-882, FRESH | 6.6 | 55 | 87.2 | 254 |
| 5 | S-882, AGED | 9.0 | 25 | 80.7 | 281 |
| 6 | S-882, AGED | 8.6 | 30 | 81.4 | 281 |
| 7 | S-882, AGED | 8.2 | 35 | 82.8 | 280 |
| 8 | S-882, AGED | 7.8 | 40 | 82.9 | 279 |
| 9 | S-882, AGED | 7.4 | 45 | 83.2 | 279 |
| 10 | S-882, AGED | 7.0 | 50 | 83.2 | 275 |
| 11 | S-882, AGED | 6.6 | 55 | 83.7 | 274 |
| Comp. 12 | S-860, FRESH | 9.1 | 25 | 80.2 | 236 |
| Comp. 13 | S-860, FRESH | 8.7 | 30 | 80.1 | 235 |
| Comp. 14 | S-860, FRESH | 8.2 | 35 | 80.3 | 233 |
| Comp. 15 | S-860, FRESH | 7.8 | 40 | 80.1 | 230 |
| Comp. 16 | S-860, FRESH | 7.4 | 45 | 80.6 | 232 |
| Comp. 17 | S-860, FRESH | 7.0 | 50 | 80.9 | 229 |
| Comp. 18 | S-860, FRESH | 6.6 | 55 | 80.8 | 229 |
| Comp. 19 | S-860, AGED | 9.1 | 25 | 77.4 | 240 |
| Comp. 20 | S-860, AGED | 8.7 | 30 | 76.9 | 240 |
| Comp. 21 | S-860, AGED | 8.2 | 35 | 76.2 | 241 |
| Comp. 22 | S-860, AGED | 7.8 | 40 | 76.0 | 240 |
| Comp. 23 | S-860, AGED | 7.4 | 45 | 76.3 | 238 |
| Comp. 24 | S-860, AGED | 7.0 | 50 | 76.2 | 240 |
| Comp. 25 | S-869, AGED | 6.6 | 55 | 75.9 | 239 |

From these results it emerges that in particular the aged S-882 catalyst is distinguished over the fresh S-882 and S-860 and the aged S-860 in that its performance (selectivity as well as activity) is clearly improved when the concentration of ethylene in the feed is raised within the range of 25 to 55 mol %.

We claim:

1. A process for the vapor phase oxidation of ethylene to ethylene oxide in the presence of a supported highly selective silver-based catalyst, at a work rate w in the range of from 32 to 320 kg ethylene oxide produced per m³ of catalyst per hour, the reaction mixture containing ethylene, oxygen, optional carbon dioxide, gas phase moderator and balance inert gases, the reaction temperature being from 180 to 325° C., the reactor inlet pressure from 1000 to 3500 kPa and the GHSV from 1500 to 10000, the process comprising:
    operating at an initial operation phase wherein fresh catalyst is used, the reaction gas mixture containing an ethylene concentration which represents an economically optimized balance between catalyst performance (expressed, at the given work rate w, by the selectivity $S_w$ in mol % and by the operating temperature $T_w$ in ° C.) on the one hand and ethylene vent losses on the other, and an oxygen concentration which complies with safety-related flammability restrictions; and
    operating at a further operation phase when the catalyst has reached an advanced aged defined by a cumulative ethylene oxide production exceeding 1.5 kT EO per m³ of catalyst, wherein in said further operation phase the composition of the reaction mixture is changed to contain from 1.1 to 4 times the concentration of ethylene used in the initial operation phase and the corresponding optimized and safe concentration of oxygen.

2. A process according to claim 1, wherein the supported highly selective silver based catalyst comprises a catalytically effective amount of silver, a promoting amount of rhenium or compound thereof, a promoting amount of at least one further metal or compound thereof, and optionally a co-promoting amount of a rhenium co-promoter selected from one or more of sulfur, phosphorus, boron, and compounds thereof.

3. A process according to claim 2, wherein the at least one further metal is selected from alkali metals, alkaline earth metals, molybdenum, tungsten, chromium, titanium, hafnium, zirconium, vanadium, thallium, thorium, tantalum, niobium, gallium, germanium and mixtures thereof.

4. A process according to claim 3, wherein the at least one further metal comprises lithium, potassium and/or cesium.

5. A process according to claim 2, wherein, calculated as the element on the total catalyst,
    the amount of silver is in the range of from 10 to 300 g/kg,
    the amount of rhenium is in the range of from 0.01 to 15 mmol/kg,
    the amount of further metal or metals is in the range of from 10 to 3000 mg/kg, and
    the amount of optional rhenium co-promoter is in the range of from 0.1 to 10 mmol/kg.

6. A process according to claim 1, wherein the support is porous and its surface area is in the range of from 0.05 to 20 m²/g.

7. A process according to claim 6, wherein the material of the support is mainly alpha alumina.

8. A process according to claim 1, wherein the gas phase moderator is 0.3–20 ppmv of an organic halide.

9. A process according to claim 8, wherein the organic halide is a $C_1$ to $C_8$ chlorohydrocarbon or bromohydrocarbon.

10. A process according to claim 9, wherein the organic halide is selected from methyl chloride, ethyl chloride, ethylene dichloride, ethylene dibromide, vinyl chloride and mixtures thereof.

11. A process according to claim 1, wherein in the further operation phase the composition of the reaction mixture is changed to contain from 5 to 30 mol % more of ethylene than the concentration of ethylene used in the initial operation phase.

* * * * *